United States Patent
Wiggli et al.

(10) Patent No.: US 10,161,780 B2
(45) Date of Patent: Dec. 25, 2018

(54) METHOD AND DEVICE FOR THE AUTOMATED CLASSIFICATION OF A LIQUID AS WELL AS METHOD AND DEVICE FOR THE AUTOMATED ADAPTION OF PRESETTINGS FOR A CAPACITIVE LIQUID LEVEL MEASUREMENT

(71) Applicant: TECAN Trading AG, Mannedorf (CH)

(72) Inventors: Markus Wiggli, Tann/ZH (CH); Nicolas Cors, Rapperswil (CH)

(73) Assignee: Tecan Trading AG, Mannedorf (CH)

( * ) Notice: Subject to any disclaimer, the term of this patent is extended or adjusted under 35 U.S.C. 154(b) by 339 days.

(21) Appl. No.: 14/683,863

(22) Filed: Apr. 10, 2015

(65) Prior Publication Data
US 2015/0292933 A1 Oct. 15, 2015

(30) Foreign Application Priority Data

Apr. 14, 2014 (CH) ...................... 0570/14

(51) Int. Cl.
*G01F 23/26* (2006.01)
*G01F 25/00* (2006.01)
*G01N 35/10* (2006.01)

(52) U.S. Cl.
CPC .......... *G01F 23/263* (2013.01); *G01F 23/265* (2013.01); *G01F 23/268* (2013.01);
(Continued)

(58) Field of Classification Search
CPC ............................ G01F 23/263; G01F 23/265
See application file for complete search history.

(56) References Cited

U.S. PATENT DOCUMENTS 3,301,056 A * 1/1967 Blanchard ............. G01F 23/266
324/607
4,115,877 A * 9/1978 Wall ......................... E04H 4/12
73/304 C
(Continued)

FOREIGN PATENT DOCUMENTS

EP 2530440 A1 12/2012
WO 2011080199 A2 7/2011

OTHER PUBLICATIONS

European Search Report dated Jun. 23, 2015, EP15158492.

*Primary Examiner* — Lisa Caputo
*Assistant Examiner* — Alex Devito
(74) *Attorney, Agent, or Firm* — Notaro, Michalos & Zaccaria P.C.

(57) ABSTRACT

A device (100) which comprises a deliverable sensor (202), a container (101) for receiving a liquid (1), a container environment (103) and a signal processing circuit (2), the input side (11) of which can be connected circuitry-wise to the sensor (102). The device (100) is designed to perform a capacitive liquid level measurement in normal operation using the sensor (102), wherein
  a threshold value can be predefined for the signal processing circuit (2) for normal operation,
  the device (100) comprises a classification module (104),
    i. which can be connected with an input side or line connection (105) circuitry-wise to the sensor (102),
    ii. which is designed to make a capacitive measurement of the liquid (1) in the container (101) using the sensor (102), and
    iii. which can be connected circuitry-wise (106) to the signal processing circuit (2) in order to trigger the specification of a threshold value using the sensor (102) for capacitive measurement of the liquid (1).

19 Claims, 9 Drawing Sheets

(52) U.S. Cl.
CPC ... *G01F 25/0061* (2013.01); *G01N 2035/103* (2013.01); *G01N 2035/1025* (2013.01)

(56) References Cited

U.S. PATENT DOCUMENTS

| | | | | |
|---|---|---|---|---|
| 4,670,219 | A | * | 6/1987 | Nelson ................... G01N 35/02 422/547 |
| 5,612,622 | A | * | 3/1997 | Goldman ............. G01N 27/025 204/400 |
| 6,164,132 | A | * | 12/2000 | Matulek ................ G01F 23/265 73/304 C |
| 2005/0161822 | A1 | * | 7/2005 | Ohkubo ................. G01K 7/015 257/758 |
| 2011/0102004 | A1 | * | 5/2011 | Schoni .................. G01F 23/266 324/750.01 |
| 2012/0024055 | A1 | | 2/2012 | Knight et al. |

* cited by examiner

•••• = Signal Intensity (SI)
━━ = Threshold value

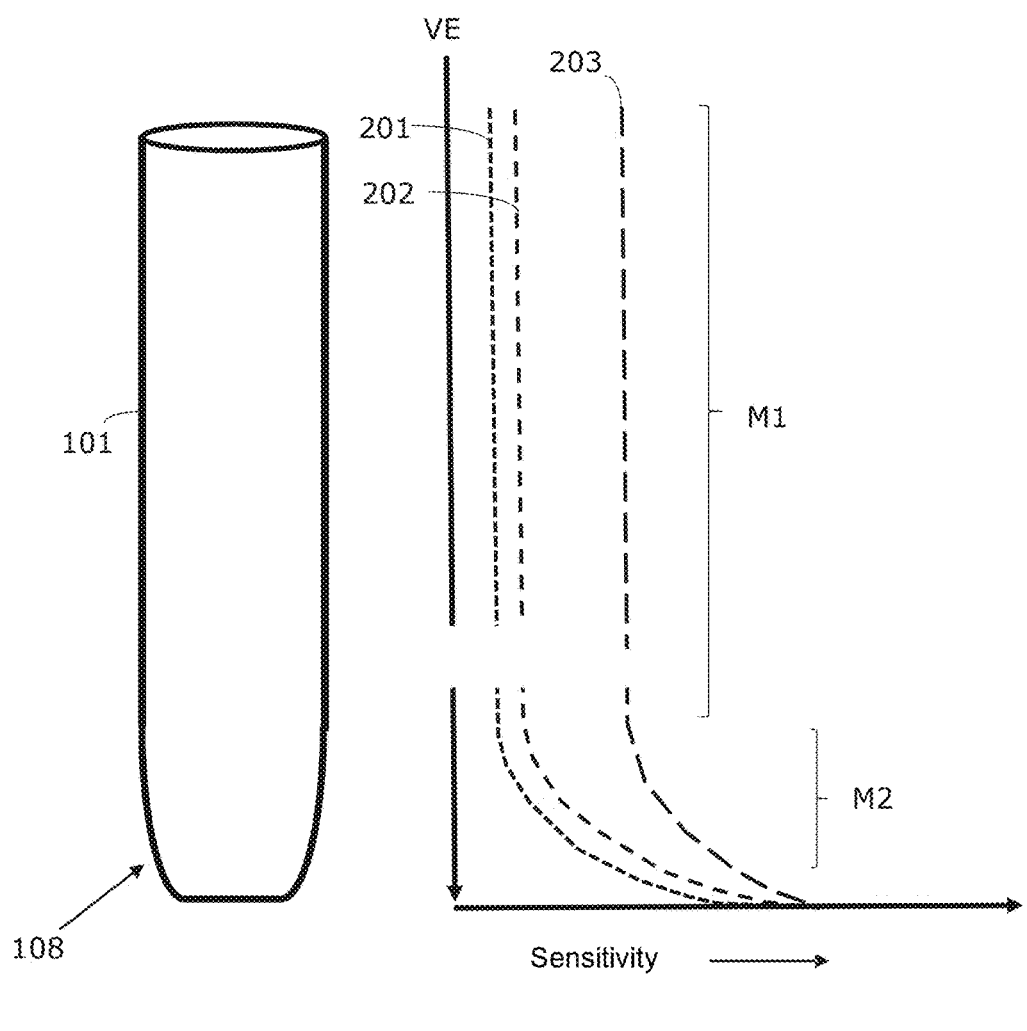

METHOD AND DEVICE FOR THE AUTOMATED CLASSIFICATION OF A LIQUID AS WELL AS METHOD AND DEVICE FOR THE AUTOMATED ADAPTION OF PRESETTINGS FOR A CAPACITIVE LIQUID LEVEL MEASUREMENT

The invention relates to methods for the automated classification of a liquid in a device which is designed to make a capacitive liquid level measurement in a container which is filled with the liquid. The invention also relates to corresponding devices.

The invention also relates to methods and devices for the automated adaptation of presettings for a capacitive liquid level measurement, where preferably the presettings are made by reference to an automated classification.

BACKGROUND OF THE INVENTION

There are numerous medical, biological, chemical and pharmaceutical devices which involve the handling and use of liquids. Thus, for example, there are automated handling systems in order to carry out medical, biological, physical and chemical investigations or to carry out processes in the corresponding technical or scientific fields.

Nowadays, most of the automated liquid handling systems are so-called computer-controlled handling systems.

A typical computer-controlled handling system comprises, for example, a work area (worktable or surface) for the placement of liquid containers, a motorized pipetting robot and a controller (usually a processor-based controller). The pipetting robot comprises at least a pipette for aspirating and dispensing liquid samples. By implementing a sequential program which is executed in the controller, the pipetting robot can be moved to a specific position in order to execute a specific handling there. Thus for example, a pipette can be lowered into a container in order to suck up a liquid there or to dispense a liquid.

Modern handling systems typically comprise means which make it possible to determine the liquid level of a liquid in a container of the handling system. The determination of the liquid level is of basic importance for a number of process sequences. For example, if one wished to prevent air accidentally being sucked in when sucking up liquid, it must be previously ensured that the pipette is immersed sufficiently far into the liquid. In order to accomplish a sufficiently far immersion in an automated sequence, the instantaneous liquid level of the liquid in the container must be determined.

There are also numerous other examples for sequences in which the liquid level of a liquid must be determined.

The liquid level of a liquid in a container can, for example, be determined by means of a capacitive liquid level measurement (also called cLLD for capacitive liquid level detection). Since a gas and a liquid have significantly different dielectric constants, the gas-liquid phase boundary can be determined by means of a change in capacitance.

The detection of a phase boundary is typically made in a capacitive manner, as shown schematically by reference to FIG. 1. FIG. 1 shows the structure of a known laboratory apparatus 10 which is here designed for detecting a liquid level. The presence of a liquid 1 in a container 5 or the phase boundary between air and liquid 1 is here detected, for example, by observing the capacitive change of $C_{tip/liq}$ and of the series capacitance $C_{coupl}$. An electronic charging/discharging circuit 2 provides for an alternate charging and discharging in order to be able to measure the effective capacitance between a sensor, e.g. in the form of a pipette tip 3 and an earthed base plate 4. The signal processing can be accomplished by means of a signal processing circuit 6 which, for example, is supported by a controller 7.

The effective capacitance, which results, depending on the laboratory apparatus 10 from the stray capacitances, electrical couplings through the sensor or the pipette tip 3, the conductivity of the liquid 1 and the crosstalk between adjacent measuring channels (referred to as next tip in FIG. 1) is very small. It is typically in the range of a few picofarad (pF). The capacitance change, which results upon plunging from the air into a liquid is once again less by approximately a factor of 100 to 1000.

Details of a device with capacitive liquid level measurement can be obtained, for example, from one of the published patent applications EP2530440A1 and WO2011080199A2 of the present applicant.

In handling systems with capacitive liquid level measurement, the user must make a basic setting so that the capacitive liquid level measurement can be made reliably and precisely by the system. It is said that the correct setting of the detection parameters must be made manually before a capacitive liquid level measurement can then be successfully made.

The setting of the detection parameters depends inter alia on physical properties of the liquid for which the liquid level is to be determined. These physical properties of the liquid to be investigated or measured are however frequently not known or only known in the form of estimated values. It is obvious that an incorrect or inaccurate specification of the detection parameters can lead to inaccurate or even incorrect detection results in the liquid level measurement.

It is now the object to provide a method which enables the automated determination and/or the automated setting of the detection parameter(s) in a handling system.

The invention relates in particular to the automated classification of a liquid and/or the application of a capacitive liquid level measurement cLLD by applying a previously made classification of the liquid.

In particular, a method and a device for the automated classification of liquids are to be provided.

A method and a device for the automated specifications of a setting or for the setting of a device is to be provided so that a capacitive liquid level measurement can be successfully carried out. A correspondingly equipped device is also to be provided.

According to the invention, a method for the automated classification of liquids in a device is provided, where the device is also designed to make a capacitive liquid level measurement in a container which is filled with a liquid.

The method of the invention comprises the following steps:
   providing the liquid in a container,
   performing a capacitive measurement of this liquid
      when executing an immersion movement of a sensor into the liquid in the container or
      when executing an emerging movement of the sensor out from the liquid in the container,
where a signal of the capacitive measurement is processed in order to make the automated classification of the liquid.

Preferably in all embodiments a signal jump of a signal of the capacitive measurement is processed, where the signal jump is produced during the immersion movement of the sensor into the liquid or during the emerging movement of the sensor out from the liquid. The automated classification of the liquid is made by means of an analysis or processing of the signal jump.

Preferably in all embodiments a liquid-specific threshold value is determined by way of the capacitive measurement of this liquid when executing the immersion movement or the emerging movement, where a signal of the capacitive measurement is processed to determine the threshold value.

Preferably in all embodiments the threshold value is related to a jump in the capacitance (signal jump) which occurs during immersion or emergence.

Preferably in all embodiments when determining the threshold value one or more of the following details or parameters or factors are specified/predefined/known:
- the type of container (geometry, wall thicknesses, material),
- the liquid volume of the liquid in the container,
- the type of sensor (e.g. fixed steel cannula, disposable pipette tips made of conducting plastic having different nominal volumes),
- the type of carrier for the container,
- the type of worktable on which the carrier is disposed.

According to the invention, an automatic classification or division of liquids into sensitivity ranges (hereinafter also designated as sensitivity classes) is made where this is accomplished by using the capacitive measurement. In this case, the classification/grouping of the liquid is made in a capacitive manner
- by means of a sensor which can be delivered into a liquid and/or
- by means of a sensor which can moved out from a liquid.

This classification/grouping of the liquid is made by determining a liquid-specific value, a liquid-specific series of discrete values or a value function which is/are related to one or more predefined threshold values or comparison criteria. The classification of the liquid into one or more sensitivity classes or groups is then made by relating to one or more predefined threshold values or to comparison criteria.

According to the invention, preferably a plurality of signal jumps or intensity values are determined and an average is formed from the signal jumps or the intensity values.

Advantageous embodiments can be deduced from the respective subclaims.

In particular, the invention relates to a method for classifying/grouping liquids in a device which comprises a capacitively operating measuring device which is designed for the detection of phase boundaries (here called capacitive liquid level measurement or cLLD for short).

By using the invention, sensitivity settings can be predefined which are suitable for making a subsequent capacitive liquid level measurement (cLLD) rapidly and reliably.

Preferably all embodiments are concerned with the automated specification of threshold values which are particularly preferably specified as adaptive threshold values.

Preferably in all embodiments the threshold values correlate with the predicted signal intensity during the immersion and/or emergence.

Preferably in all the embodiments the threshold values have a dependence on the liquid volume which is to be detected by means of cLLD.

Particularly preferably in all the embodiments the threshold values have a dependence on the size of the interface which is obtained between the liquid to be measured and the container, i.e. a dependence on the so-called wetted area.

Preferably in all embodiments the sensitivity setting can be tracked and/or adapted dynamically where this is accomplished particularly preferably as a function of the wetted area.

Preferably in all embodiments two or three sensitivity groups are predefined where each of these groups has its own specific sensitivity profiles as a function of the liquid volume and/or the wetted area.

Particularly preferred are embodiments in which each of the sensitivity classes has its own specific threshold value profile (adapted to or derived from the sensitivity profile).

The shape (geometry) of the container and the liquid volume to be detected are also relevant. Therefore preferably in all embodiments the sensitivity is dependent on the shape (geometry) of the container or the wall surface which is covered by the liquid (called wetted area).

The threshold value(s) which has/have been assigned as liquid-specific values of a liquid or the classification or grouping of a liquid can be applied according to the invention, for example, in other system arrangements or configurations, by for example converting the threshold values or by retrieving corresponding entries from a table or a memory by means of a table enquiry. This principle can be applied to all embodiments of the invention.

The threshold value(s) which has/have been assigned as liquid-specific values of a liquid or the classification or grouping of a liquid can be used in connection with other labware. This principle can be applied to all embodiments of the invention.

In preferred embodiments of the invention, one or more of the following statements/rules is implemented:
- the sensitivity is not a constant;
- the sensitivity depends at least on the liquid volume to be detected and/or on the wetted area (possibly also on other parameters);
- preferably a different sensitivity or sensitivity curve is predefined depending on liquid volume and/or the wetted area;
- preferably the classification into sensitivity classes is made according to the intensity of the capacitance jump during immersion or emergence of the sensor;
- a suitable threshold value, a suitable series of threshold values or a suitable threshold value function is predefined by means of the sensitivity class;
- a different series of threshold values or a different threshold value function is applied depending on the sensitivity class of the liquid (i.e. depending on the conductivity and permittivity).

The precise presetting of the sensitivity for a liquid to be measured is particularly important since capacitive liquid level measurements (cLLD) are very sensitive. An incorrect setting can lead to incorrect or very inaccurate results. The invention offers a higher reliability in cLLD as a result of the automated classification.

For successful capacitive liquid level measurements (cLLD), the selection or specification of a suitable sensitivity setting is therefore made possible according to the invention, preferably in all embodiments. Preferably the specification of a suitable sensitivity setting is carried automatically by the device in all embodiments.

It is an advantage of the invention that the user of a device need not be concerned about detailed information of the liquids which are to be used. In addition, he preferably need not make any manual inputs in any of the embodiments since the device of the invention is designed to automatically classify one or more liquids, e.g. after retrieving a corresponding procedure and/or to predefine the presetting(s) for a subsequent capacitive liquid level measurement (cLLD).

The invention in all embodiments makes the configuration sequence and the handling of such devices simpler and less liable to error.

The invention, depending on implementation, enables a more intelligent detection and reaction to errors when carrying out a capacitive liquid level measurement (cLLD).

The invention enables the mechanical and physical limits of present-day liquid handling systems to be further advanced and go to the smallest volumes.

The capacitive liquid level measurement (cLLD) of the invention functions with any current labware (container) such as microplates with wells, plastic or glass tubes and trays.

Preferably in all embodiments special carriers are used for receiving or carrying the labware (containers) which are optimized for a capacitive liquid level measurement (cLLD). Such a carrier should fulfil one or more of the following criteria:

- the carrier walls are designed to be non-conductive;
- the carrier base is designed to be conductive and earthed (for example, together with the worktable);
- the carrier base is designed so that it is located near the liquid.

The invention preferably in all embodiments carries out a capacitive liquid level measurement (cLLD) with evaluation of a fast and a slow signal, where different threshold values are used to evaluate the fast signal and for the slow signal. In this case, at least one of the two threshold values (preferably both threshold values) has a dependence on the liquid volume that is to be detected and/or a dependence on the area wetted instantaneously by the liquid to be measured.

The physical properties of a liquid need not be known in any embodiment of the invention.

The invention in all embodiments offers a higher reliability of the capacitive liquid level measurement (cLLD) as a result of the automated classification carried out previously according to the invention.

The invention enables a more intelligent detection and reaction to errors.

With the invention it is possible to detect smaller volumes within the framework of the capacitive liquid level measurement (cLLD) than previously (e.g. up to about 2 μl tap water in a well with a V-shaped base of a 384-well microplate).

With the invention it is also possible to detect smaller volumes within the framework of the capacitive liquid level measurement (cLLD) of poorly conducting liquids (e.g. up to about 30 μl ethanol in a well with a V-shaped base of a 384-well microplate).

In all embodiments, in most cases a single cLLD detection is sufficient, i.e. a measurement need not be repeated. This applies particularly if, as mentioned, one fast and one slow signal is used in the capacitive liquid level measurement (cLLD).

The handling systems (devices) according to the invention and the methods according to the invention are now explained in detail by means of schematic drawings of exemplary embodiments which do not restrict the scope of the invention.

FIG. 8A shows a highly schematic diagram which is related to a container shown on the left where a curve is predefined for each of three liquid classes in the diagram;

Exemplary liquid handling systems 100 are described hereinafter, where the invention can however easily also be applied to other handling systems, laboratory systems, medical and pharmaceutical systems and the like. These systems are designated overall here as devices 100.

The term container 101 (also called labware) comprises inter alia the following containers: microplates with wells, trays, tubes (made of glass or plastic), containers, bottles, flasks and the like.

Figure 4A:
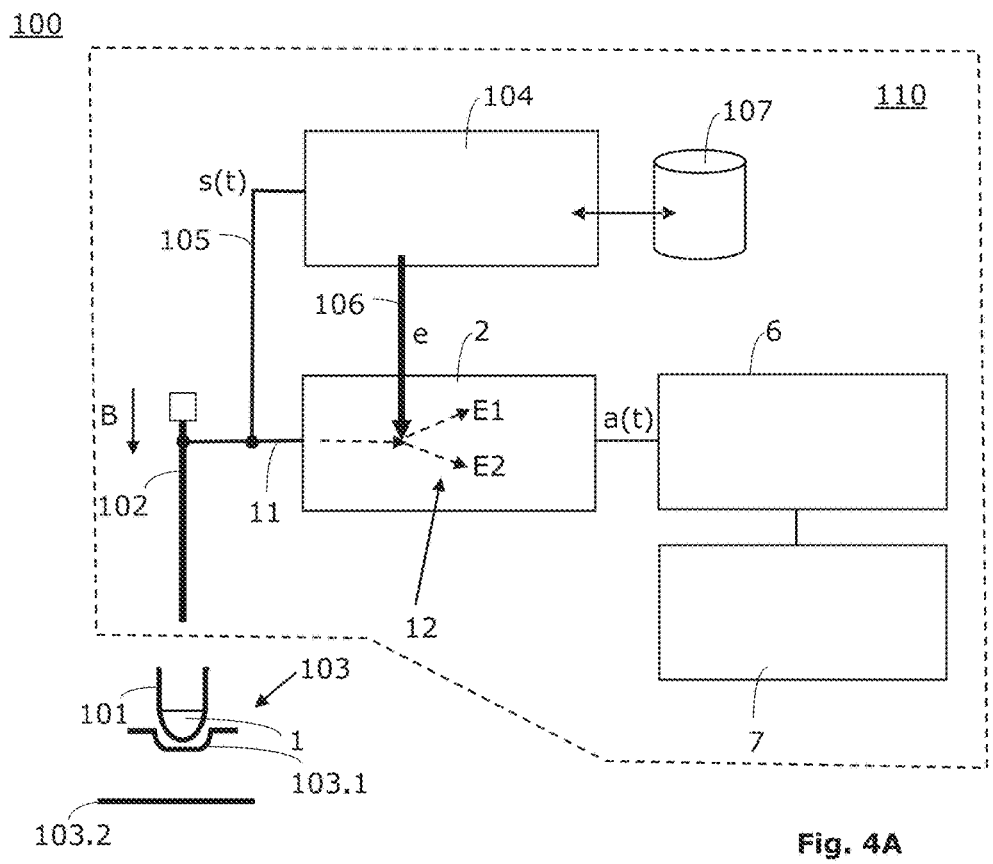
FIG. 4A shows a schematic view of a first device according to the invention which on the one hand is designed for carrying out a capacitive measurement and classification of a liquid and on the other hand for carrying out a capacitive liquid level measurement (cLLD)
Figure 4B:
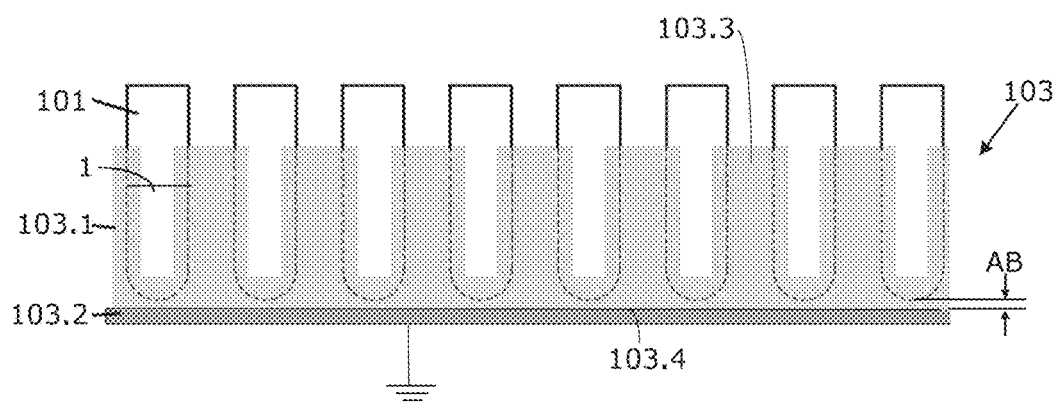
FIG. 4B shows a schematic view of a part of another device according to the invention which comprises an earthed worktable on which a carrier with 8 tubes is disposed.
Figure 4C:
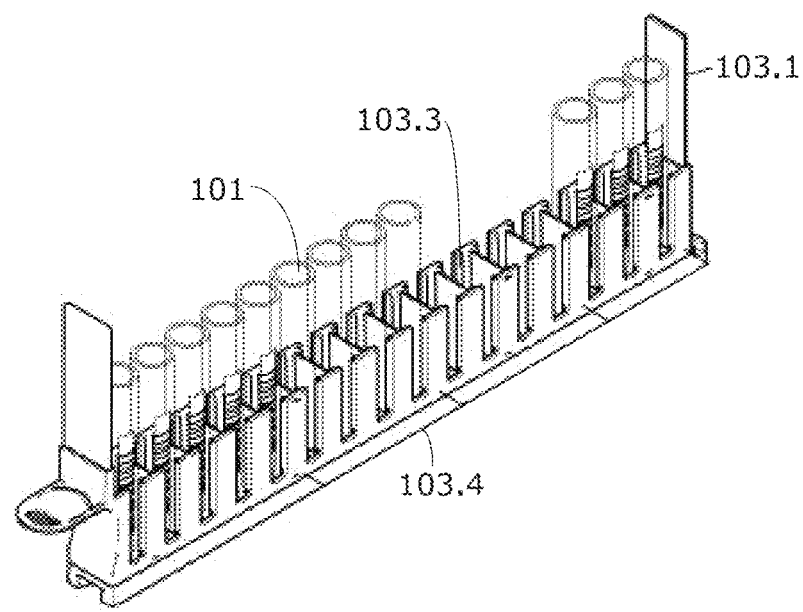
FIG. 4C shows a perspective view of an exemplary carrier which is here fitted with 12 tubes.

In addition, each container 101 is assigned a carrier 103.1 (here also called carrier 103.1) on which or in which the container 101 can be disposed, as shown in schematic form in FIGS. 4A, 4B and 4C by reference to several examples.

When in the following there is talk of a type of sensor 102, a type of container 101, a type of carrier 103.1 or a type of worktable 103.2, the word "type" should then comprise the geometry and the material.

The carrier 103.1 is located above a worktable 103.2 or another suitable surface as can be seen for example in FIG. 4B.

The worktable 103.2 together with the carrier 103.1 is here designated as container environment 103.

In order to enable a reliable and repeatedly accurate determination of the liquid level by means of capacitive liquid level measurement cLLD, the liquids 1 to be measured are divided into different sensitivity groups or classes. This process is here also designated as classification (or grouping) of a liquid 1. This classification is preferably carried out in all embodiments by means of the direct or indirect measurement of the conductivity and effective static permittivity of the respective liquid 1.

Investigations have revealed that within the framework of the invention no absolute measurement or determination of the conductivity and the permittivity are required. A qualitative assessment of the liquids 1 is sufficient for all embodiments.

The conductivity and permittivity are specific material properties which are used here indirectly for classifying liquids 1 by means of a capacitive measuring process (called capacitive measurement) which operates in a summarizing (integrating) manner.

The permittivity of matter, here of a liquid 1, (usually specified as $\in$) designates the dielectric conductivity of the matter. The unit is typically As/Vm. The permittivity is frequency-dependent. It is, for example, very strongly defined in water.

The permittivity can also be represented as a product of the frequency-dependent permittivity $\in(\omega)$ (also called relative dielectric constant) and the field constant $\in_0$ (dielectric constant of vacuum).

The specific magnitude of the conductivity for a predefined geometry of a measuring arrangement is linked via the admittance Y to the complex frequency-dependent impedance. The conductivity can therefore be recorded directly by measurement techniques in a device 100 of the invention.

"Siemens/μm" (S/μm) is used as the unit for the conductivity. Example: highly pure water has 0.05 μS/cm to 0.1 μS/cm and tap water has 300 μS/cm to 1 mS/cm.

Preferably in all embodiments a capacitive measurement is carried out (see step S1 in FIG. 3) in order to then relate the liquid 1 or compared with predefined (e.g. with previously determined) reference quantities, which can be provided, for example, from a memory 107 (see FIG. 4A).

Figure 3:
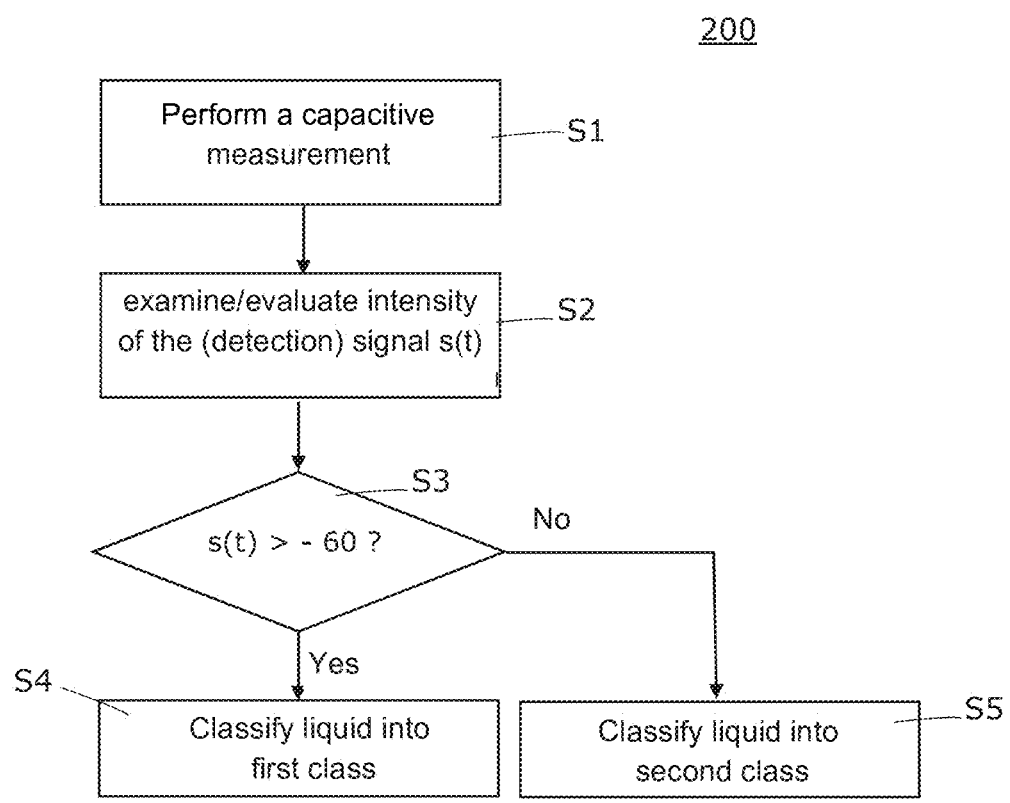
FIG. 3 shows a schematic flow diagram of a first exemplary method of the invention.

The classification is made in all embodiments by means of a capacitive measurement (see step S1 in FIG. 3). Preferably this capacitive measurement is made during immersion or emergence of a sensor 102. However, a capacitive measurement can also be carried out whilst the sensor 102 is located in the liquid 1. In the latter case, an absolute measurement is made in order to be able to classify the liquid 1.

Within the framework of the invention, preferably in all embodiments the same capacitive liquid level measurement system 110 which is also used subsequently for detecting the liquid level is used to determine the sensitivity group or class or to classify the liquids 1.

Preferably in all devices 100 therefore one and the same liquid level measurement system 110 is used both for classifying liquids 1 and also for detecting the liquid level. This has the advantage that the results of the automated classification can be readily transferred and applied to the capacitive liquid level measurement.

Preferably in all embodiments a special classification module 104 is used which enables an influencing or adjustment of the (measurement) sensitivity of a charging/discharging circuit 2 and/or a signal processing circuit 6 via a circuitry-wise connection or link 106, as indicated in FIG. 4A.

According to the embodiment, the classification module 104 can predefine the threshold values corresponding to the circuits 2 and/or 6, threshold value series or a threshold value function sV(FV) or sV(bO) or it can, for example, trigger the specification of a threshold value, a series of threshold values or a threshold value function sV(FV) or sV(bO) by means of a signal or a quantity e.

The functional groups or assemblies of FIG. 4A can be partially or all combined together in one circuit where such a circuit is preferably a processor-controlled circuit which comprises at least one processor which processes instructions/commands from a memory.

In this case and in other embodiments which comprise a processor, there is talk here of a processor-based implementation. Such an implementation comprises a combination of hardware and software.

Within the framework of the invention preferably in all embodiments frequency-dependent conduction processes are measured in the liquid system to be investigated by capacitive methods. This process is here designated as capacitive measurement (step S1 in FIG. 3). Compared with a resistance measurement of the liquid 1 using a direct current, the capacitive measurement of the impedance yields a substantially more informative complex quantity Z or the jump of a complex quantity Z. The embodiments of the invention are therefore based on a capacitive measurement which uses an alternating voltage (AC voltage). In all embodiments of the invention, this alternating voltage can be provided, for example, by a charging/discharging circuit 2 and applied to the sensor 102. The sensor 102 is in this case charged with a low potential. During immersion into or emergence from the liquid 1, an abrupt change in the capacitance is obtained which can be measured or evaluated (e.g. by the circuit 104 or 6).

When performing the capacitive measurement, the measurement or evaluation is accomplished, for example, by the classification module 104. When performing the capacitive liquid level measurement, the measurement or evaluation is made, for example, by the signal processing circuit 6. However, both can also be made in a common circuit module.

An ideal sensor geometry for characterizing the material properties of a liquid 1 comprises a homogeneous electric field in the liquid 1 to be studied with negligible edge effects and stray field capacitances. This requirement is only fulfilled by two plane-parallel electrode plates of infinite extension between which the liquid 1 is disposed. In a real device 100 the environment is significantly different. Investigations have shown that by means of a linearly deliverable sensor 102 in the real environment of a container 101, sufficiently accurate determinations can be made within the framework of a capacitive measurement to enable a classification. In particular, it has been shown that such capacitive measurements are sufficient in order to classify the liquids 1 to be studied into one of several (preferably three) sensitivity groups or classes.

Compared to dielectrics, liquids exhibit a very complex behaviour in the solid phase. In the liquid phase various charge transport processes as well as reversible and irreversible electrochemical reactions can occur depending on frequency and amplitude of an acting electric alternating field and the temperature. Thus, within the framework of the invention a frequency band of 200 kHz to 500 kHz and preferably of 250 kHz to 350 kHz is selected for the capacitive measurement in order to avoid electrochemical reactions in the liquid 1 to be studied as far as possible.

Preferably in all embodiments the same frequency band is used in the automated classification as in the capacitive liquid level measurement cLLD. Thus, preferably the same circuit 2 can be used in both processes.

The amplitude of the alternating voltage (AC voltage) to be applied to the sensor 102 is obtained from the requirement for a suitably large signal-to-noise ratio. Preferably in all embodiments of the invention, the applied alternating voltage has a charge curve which ends at about 5 V depending on the sensor geometry used.

Preferably in all embodiments the same amplitude is used in the automated classification as in the capacitive liquid level measurement. Thus, preferably the same circuit 2 can be used in both processes.

Preferably in all embodiments the same direct voltage fraction (polarization voltage) is used in the automated classification as in the capacitive liquid level measurement. The direct voltage fraction (polarization fraction) is preferably about 3 V.

The procedure for determining the sensitivity group or class or for classifying a liquid 1 preferably comprises the following steps:

providing a (defined) liquid volume FV of the liquid 1 to be classified. This is preferably accomplished in all embodiments in a defined container 101, i.e. in a container 101 of previously specified type.

A (defined) sensor 102, preferably a sensor 102 of previously specified type, is delivered into the (defined) liquid volume FV of this liquid 1 (called immersion movement) and a capacitive measurement of the liquid 1 is performed (in this case) with a previously suitably adapted sensitivity or with the maximum sensitivity. In this case, preferably in all embodiments a defined measurement environment is used. Such a defined measurement environment preferably comprises at least one defined container 101 (here also designated as dedicated container) and a defined carrier 103.1.

By means of a (detection) signal s(t), which is provided by the sensor 102 during the capacitive measurement of the liquid 1, the liquid 1 is classified into one of several sensitivity groups or classes. Preferably all the embodiments use a signal jump of the (detection) signal s(t) or the intensity of the (detection) signal s(t) of the capacitive measurement in order to perform the classification into a sensitivity group or class. Preferably in all embodiments the classification into a sensitivity class is made by relating the intensity of the (detection) signal s(t) to at least one predefined threshold value. If the intensity of the (detection) signal s(t) lies above the predefined threshold value, this liquid is classified into a first sensitivity class (step S4 in FIG. 3). If the intensity of the (detection) signal s(t) lies below the predefined threshold value, this liquid is classified into a second sensitivity class (step S5 in FIG. 3).

The classification of the liquid 1 thus made into a specific sensitivity group or class is then used (immediately or subsequently) in a capacitive liquid level measurement cLLD in order to predefine the suitable sensitivity (pre)setting for this liquid level measurement.

The capacitive measurement of the liquid 1 is preferably made in all embodiments by the device 100 performing the capacitive measurement with the highest sensitivity. By means of the signal intensity measured with the highest sensitivity and the predefined threshold values, the liquid is classified into one of several sensitivity groups or classes.

Preferably the capacitive measurement of the liquid 1 is performed successively in the same tube 101 using, for example, all eight sensors of a laboratory apparatus 100 provided with pipette tips of the same type 102 (e.g. a 200 disposable tip 102 can be used eight times). The first of the eight measurements is preferably discarded since it is frequently falsified by electrostatic effects. From the remaining seven measurements preferably in all embodiments the median of the measured signals is determined and the classification is performed on the basis of this median.

FIG. 4A shows that a classification module 104 is connected circuitry-wise to the charging/discharging circuit 2 in order to connect the automated classification to the execution of the capacitive liquid level measurement.

In all embodiments the classification module 104 can however also be only connected circuitry-wise to the signal processing circuit 6 or to both circuits 2 and 6.

According to the invention, the classification of a liquid 1 into a specific sensitivity group or class also enables a capacitive liquid level measurement cLLD to be made in a different environment (e.g. in a different container 101 or in a different platform or device 100).

By means of the specific sensitivity group or class, a computational adaptation can be made to a different liquid volume FV and/or to a different wetted area and/or to a different container 101 and/or to a different carrier 103.1 and/or to a different worktable 103.2 and/or to a different pipette tip 102. In this case the device 100 comprises a module or the device 100 can be connected to a module which performs a computational adaptation before one of the two circuits 2, 6 or both circuits 2, 6 are then set or reset accordingly for a liquid level measurement cLLD.

Preferably all the embodiments are designed so that they are capable of identifying or eliminating liquids 1 which are not suitable for a capacitive liquid level measurement in the device 100. The identification or elimination can be made, for example, if the capacitive measurement of a liquid 1 gives a (detection) signal s(T) which does not allow any classification because, for example, it lies below a minimum value (lower threshold value).

Figure 1:
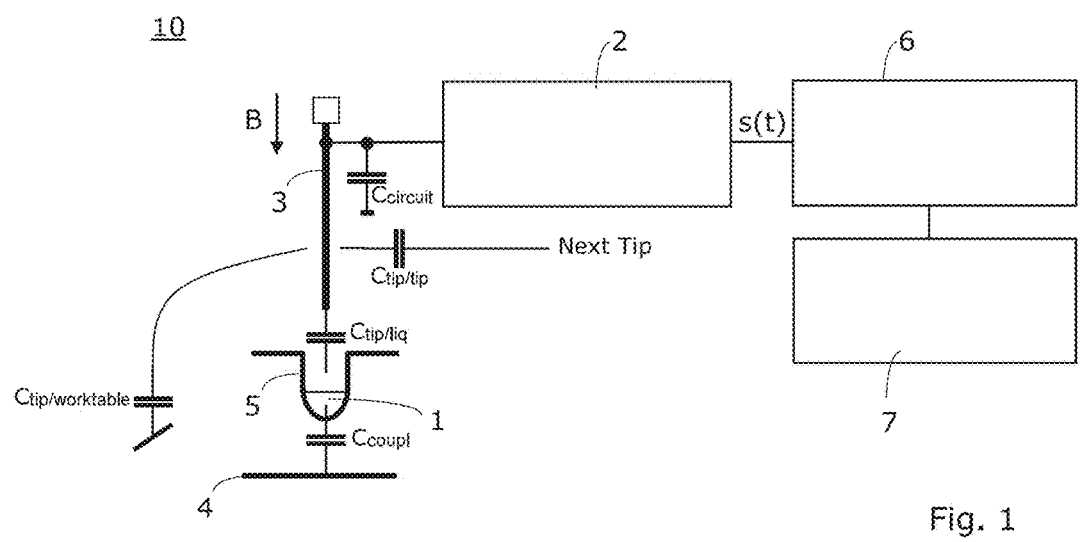
FIG. 1 shows a schematic view of a laboratory apparatus according to the prior art.
Figure 2:
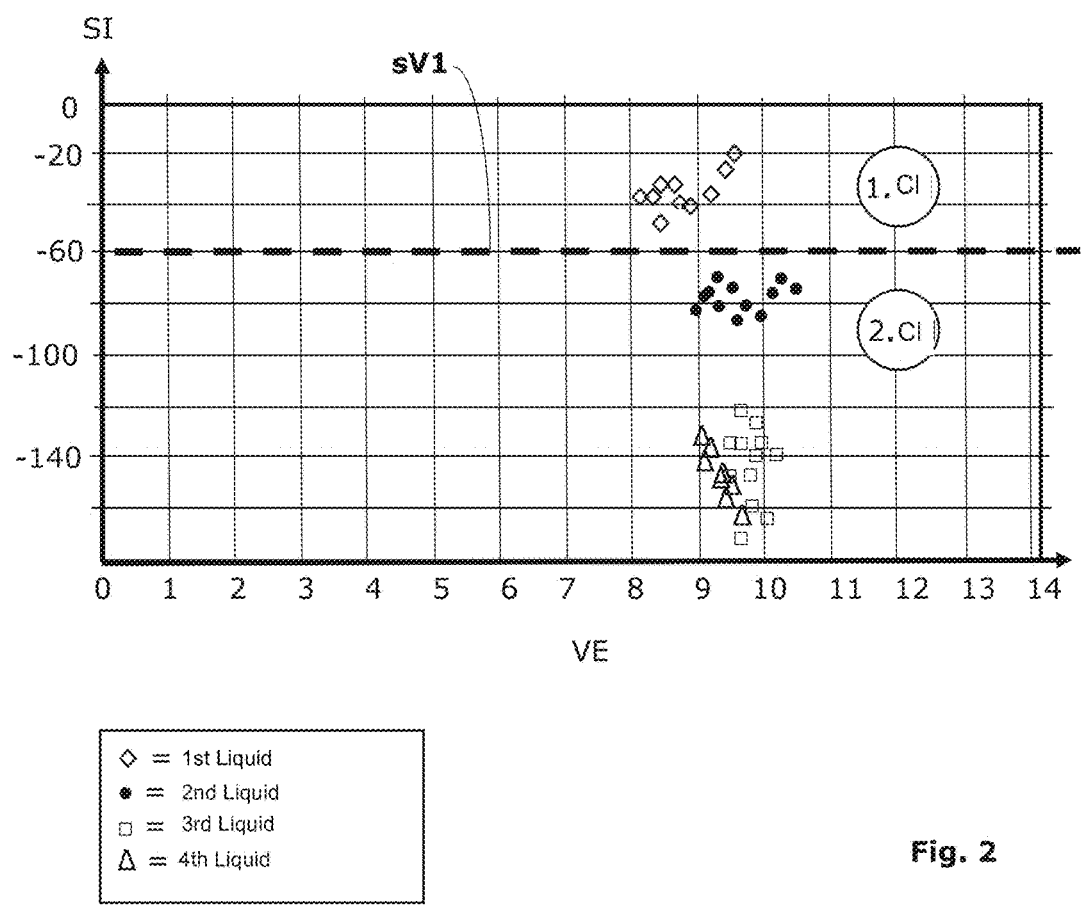
FIG. 2 shows a schematic graph with the results of measurements according to the invention of four different liquids in an Eppendorf Tube®.

FIG. 2 shows a graphical diagram of measurements which were conducted using four different liquids in a device 100 of the invention. Each of the four liquids is assigned a different graphical signal as shown in the legend to FIG. 2. The first liquid here comprises EtOH (ethanol), the second liquid comprises diwater (distilled and de-ionized water), the third liquid comprises tap water and the fourth liquid comprises 3-molar NaCl (sodium chloride).

FIG. 2 reveals that the first and second liquids can be clearly distinguished if the (signal) intensity SI of the (detection) signal s(t) is examined. The third and fourth liquids can be distinguished less clearly by an examination of the intensity SI, where in each case these third and fourth liquids can in turn be clearly distinguished from the first and second liquids. Here so-called volume units VE are plotted on the x axis (e.g. in 10 μl steps).

FIG. 3 shows a schematic diagram of a preferred method 200 of the invention. The method 200 is divided in the exemplary embodiment shown into five steps which are characterized by S1 to S5.

In the first step S1 a capacitive measurement of a liquid 1 is made. This capacitive measurement can be carried out when executing an immersion movement of the sensor 102 into the liquid 1 or when executing an emerging movement of the sensor 102 from the liquid 1. The capacitive measurement yields a (detection) signal s(t) which is preferably processed in all embodiments by a separate or integrated classification module 104 (see FIG. 4A).

Preferably in all embodiments within the framework of step S2, a signal jump of a signal s(t) of the capacitive measurement which is obtained during the immersion movement of the sensor 102 into the liquid 1 or during the emerging movement of the sensor 102 from the liquid 1 is processed or examined in order to perform the automated classification of the liquid 1.

In the second step S2, for example, the intensity (signal strength) of the (detection) signal s(t) in the area of the signal jump is examined/determined and in step S3 a classification or grouping is performed by means of a predefined threshold value (e.g. sV1) which in the example shown here lies at −60. In the diagram in FIG. 2, no unit for the intensity SI was intentionally predefined since this unit depends on the specific circuitry-wise implementation. In a similar circuitry-wise arrangement the signal intensity SI can be given e.g. in mV. In a digital circuitry-wise arrangement, the signal intensity SI can be given, for example, in ADU. ADU stands for analog-digital conversion and designates the number of quantification steps which were used to quantify the analog (detection) signal s(t).

In FIG. 2 the point cloud of the first liquid lies in the range between −50 and −18 whereas the point cloud of the second liquid lies in the range between −90 and −70. A threshold value sV1 was predefined as −60. This threshold value (e.g. sV1) is interrogated in step S3. If the measured intensity of the (detection) signal s(t) lies above −60, the corresponding liquid is classified into the first sensitivity class (called 1st Cl.). Otherwise the liquid is classified into a second sensitivity class (called 2nd Cl.). Another threshold value could be specified, e.g. at −100. Now, another step could be added, for example, to step S3 which checks whether the measured intensity of the (detection) signal s(t) is less than −100. If this is the case, it can then be ascertained, for example, that this liquid is not suitable for a capacitive liquid level detection in the device 100.

Accurate investigations show that there can be various factors which have an influence on the classification of the liquids. If such influences are present, these are taken into account according to the invention when performing the measurements and/or when evaluating the measurements. Among others, the following (environmental) influences can play a role:
  the liquid volume FV of the liquid 1 in the container 101,
  type of container 101 (material and geometry),
  type of sensor 102 (material and geometry),
  type of carrier 103.1 (material and geometry),
  type of worktable 103.2 (material and geometry).

The instantaneously wetted surface area can be determined in each case from the instantaneous liquid volume FV of the liquid 1 in the container 101 and from the geometry of the container 101, if necessary. Or conversely the sensitivity can have a dependence on a curve or series of values which is related to the wetted surface area, i.e. in such a case there is a dependence of the threshold value Sv(bO) on the wetted surface area.

In addition, the wiring e.g. of the carrier 103.1 and of the worktable 103.2 plays a role. Through earthing, for example, they can both be at the same potential, which is advantageous. FIG. 4B shows a schematic example, in which a container 101 with a round base rests in a carrier 103.1 which sits on a worktable 103.2. The worktable 103.2 and/or the carrier 103.1 can be earthed. Preferably in all embodiments the worktable 103.2 is earthed (as shown in FIG. 4B) and the carrier 103.1 comprises a non-conducting material (e.g. plastic). An earthed container environment 103 is particularly suitable.

The automated classification of the liquid 1 can be accomplished in all embodiments of the invention in a predefined classification environment of the device 100. Such a predefined classification environment is characterized in that at least one of the following specifications is identical to the specifications (determination environment) which are used when determining the predefined threshold values (e.g. T1):
  the liquid volume FV of the liquid 1 in the container 101 or the wetted surface area between the liquid 1 and the container 101,
  the type of sensor 102,
  the type of container 101 (preferably a dedicated container is used),
  the type of carrier 103.1,
  the type of worktable 103.2, on which the (dedicated) carrier 103.1 is disposed.

If the wetted surface area between the liquid 1 and the container 101 is known, the type of container 101 and the liquid volume FV need not necessarily be known since the wetted surface area is dependent on the type of container 101 and on the liquid volume FV.

The present invention makes it possible to classify or distinguish e.g. containers 101, when the capacitive measurements are made with a known (predefined) liquid, a known (predefined) liquid volume FV and a known (predefined) sensor 102 in an otherwise known environment 103. In this case, a classification or distinction, e.g. of the containers 101 can be made, for example, by means of the intensity of the signal s(t). Thus, for example, (cLLD) suitable containers 101 could be automatically distinguished from unsuitable ones.

Preferably all embodiments of the device 100 are equipped with automated measurement procedures which are designed to classify or distinguish
  containers 101 and/or
  carriers 103.1 and/or
  worktables 103.2 and/or
  sensors 102.
In this case, in a device 100 which is equipped with a corresponding measurement procedure, it is, for example, possible to determine in which type of container 101 a liquid 1 is located or, for example, which type of sensor 102 (which sensor type) is used currently.

The present invention also makes it possible to distinguish between various liquids 1 which are (should be) used in the device 100 if these different liquids 1 can be distinguished by means of their permittivity and conductivity. Such a distinction between different liquids 1 can be made without the previously described classification. For such a distinction it is merely sufficient to make a comparative capacitive measurement, i.e. it is sufficient in this case if relative measurements are made. If it is known, for example, that in a device 100 only ethanol is present as first liquid and distilled de-ionized water is present as second liquid, these two liquids can be distinguished by means of an intensity examination of the signals s(t). In this way, confusions of liquids 1 can be avoided in an automated sequence.

Preferably all embodiments are equipped with a measurement procedure which is suitable for distinguishing different liquids 1.

Influences which can be produced by spatial inhomogeneities of the temperature, the pressure and the liquid concentration or by a perturbing field are not considered here. In order to achieve a high reproducibility however, as far as possible the essential aspects which can have an influence should be specified.

Preferably in all embodiments, the determination of a liquid-specific value is made. This liquid-specific value can be derived, for example, by means of the intensity of the signal s(t) (e.g. obtained by a table enquiry from a table or determined by circuitry) or it can be calculated or derived from the intensity of the signal s(t). This liquid-specific value, if present, preferably in all embodiments can be used for the precise setting of the threshold value(s) for the subsequent capacitive liquid level measurement cLLD in the device 100. In this case, the liquid-specific value(s) are made available to the circuit 2 and/or 6 before carrying out a capacitive liquid level measurement cLLD. The circuit 2 and/or 6 is then automatically preset to a suitable sensitivity (e.g. E1 or E2) by predefining the threshold value(s) for the capacitive liquid level measurement cLLD.

Depending on the embodiment, the presetting of the sensitivity can be made by specifying one or more threshold values sV1, sV2 or a threshold value function sV(FV) or sV(bO) by the circuit 2 and/or 6 or the presetting can be made by a signal or a control variable which is transmitted or provided by the classification module 104 via a connection 106 to the circuit 2 and/or 6, as shown in FIG. 4A. In FIG. 4A it is indicated that the circuit 2 can comprise an influenceable switch or an actuator 12 which can be switched/converted directly or indirectly by the signal or the control variable.

If (only) a classification of the liquid 1 into a class has been made, as shown for example in FIG. 3, the setting of the threshold value(s) for a subsequent capacitive liquid level measurement cLLD in the device 100 can be made by means of the assignation to a specific class. Each such class can then be assigned, for example, a constant threshold value (e.g. sV1). If therefore, for example, in a liquid 1 in the device 100 a liquid level measurement cLLD is to be made, the assignation of the liquid 1 to a specific class is examined in order to make the setting of the threshold value(s) according to this class.

Preferably the device 100 of the invention comprises a (changeover) switch or an actuator 12 (as already mentioned) in order to automatically set the suitable threshold values before a liquid level measurement cLLD is made. The set threshold values can be constant. Preferably in all embodiments they have a dependence on the liquid volume FV (therefore designated as sV(FV)) or they have a dependence on the wetted surface area (therefore designated as sV(bO).

FIG. 4A shows an exemplary implementation of a device 100 which according to the invention is equipped with an already mentioned module 104, which is designed for automated classification of a liquid 1 within the device 100. The module 104 can, as shown in FIG. 4a, be connected directly to the sensor 102 via a line connection 105. If a capacitive measurement (step S1 in FIG. 3) is performed, the module 104 determines, for example, the intensity of the signal s(t) which was tapped at the sensor 102 (e.g. during execution of an immersion movement) or other properties of a signal jump. Then, for example, the liquid 1 located in the container 101, is classified into one of two different sensitivity classes. If now at a later time point in the device 100 a liquid level measurement cLLD of the liquid 1 is to be performed in the container 101 (or in another container), the module 104 influences the setting of the threshold value(s) of the charging/discharging circuit 2 (and/or of the circuit 6). FIG. 4A shows an embodiment in which a (changeover) switch or an actuator 12 enables the switchover from a first sensitivity E1 to a second sensitivity E2 (or conversely). The higher the sensitivity, the lower the corresponding threshold value is set and conversely.

According to the invention, in all embodiments of the invention the sensitivity can be predefined (depending on the previously accomplished classification of the liquid 1), in order to be able to predefine the corresponding signals (e.g. the amplitude of the alternating voltage and/or the frequency) during charging/discharging of the sensor 102 by the charging/discharging circuit 2 and/or in order to make a corresponding setting of the sensitivity (e.g. by adapting an amplification factor in the circuit 6) when evaluating/processing the signal a(t) (e.g. by the circuit 6).

In this way a "usable" (e.g. a signal having few perturbing influences) output signal a(t) of a liquid level measurement cLLD by the charging/discharging circuit 2 is provided which can be further processed and evaluated in a subsequent signal processing circuit 6.

The sequence of the process 200 can, for example, be triggered and/or monitored by the controller 7 of the device 100. The module 104 can however also have its own controller (processor) for the sequence control of the process 200.

Both when executing the capacitive measurement and also during a liquid level measurement cLLD the signal which can be tapped at the sensor 102 during immersion and during emergence makes a signal jump. During immersion the signal has a different sign to that during emergence. Preferably during the automated classification of a liquid 1 and also when executing a liquid level measurement cLLD the jump height or the amplitude is evaluated. Here therefore there is talk of the signal intensity SI of the signal s(t) in the range of the signal jump.

As already mentioned, the automated classification of the liquid 1 preferably in all embodiments is made with the aid of desired values which (e.g. in a predefined determination environment of the device 100) were determined and then stored (e.g. in a memory 107, see FIG. 4A). Since desired values can be used for assistance, the invention operates with qualitative or relative predictions. If, for example, the signal jump is greater than sV1=−60, the corresponding liquid 1 is classified into first class, etc.

In all embodiments within the framework of the capacitive measurement a faster signal $s1(t)$ and a slower signal $s2(t)$ can be derived/obtained from the (detection) signal and processed. From these two signals $s1(t)$ and $s2(t)$ a first threshold value sV1 for the fast signal $s1(t)$ and a second threshold value sVl for the slow signal $s2(t)$ are determined. This procedure is optional.

Figure 5:
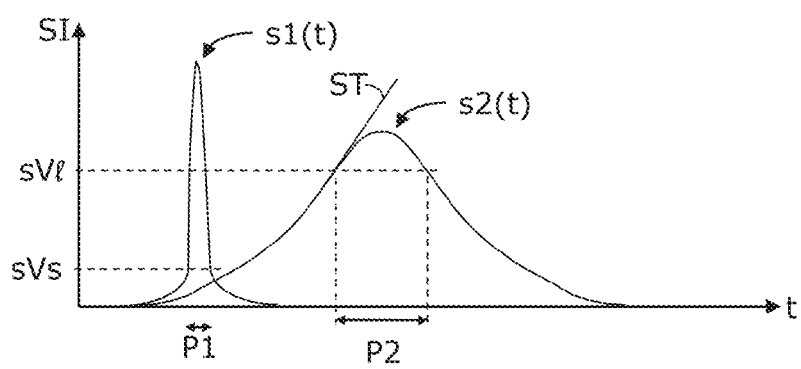
FIG. 5 shows a schematic intensity-time diagram in which two signals according to the invention of a capacitive liquid level measurement (cLLD) are presented in simplified form in order to be able to describe the application of two different threshold values (and possibly other criteria) according to a further embodiment.

FIG. 5 now show a liquid level measurement cLLD which is based on the processing of a faster signal $s1(t)$ and a slower signal $s2(t)$. In FIG. 5 the behaviour of the signal intensity SI of the two signals is plotted over the time t. In addition, the position of the two threshold values vSs and vSl is shown. If the signal $s1(t)$ exceeds the first threshold value vSs, this can be seen as a first positive indication for the immersion or emergence (depending on the sign). Now if the signal $s2(t)$ exceeds the second threshold value vSl (here with vSl>vSs), this can be seen as definitive confirmation for the immersion or emergence (depending on sign).

In practical applications, in addition to these two threshold values vSs, vSl preferably other criteria (here the pulse width P1 of the first signal $s1(t)$ and the slope ST of the second signal $s2(t)$) are evaluated to check the correctness of the detection.

According to the invention, during the automated classification of the liquid 1 at least two different threshold values vSs, vSl and preferably other criteria (P1, ST) can be determined and stored for a subsequent use in a liquid level measurement cLLD. The threshold values vSs, vSl in preferred embodiments have a dependence on the liquid volume FV and/or on the wetted surface area.

In all embodiments for a subsequent liquid level measurement cLLD with fast signal $s1(t)$ and slow signal $s2(t)$ the threshold values vSl of the slow signal $s2(t)$ can be determined from the threshold values vSs of the fast signal $S1(t)$ or conversely.

Embodiments are described hereinafter in which the threshold value(s) are not constant. These embodiments are based on the finding that there is a dependence on the liquid volume FV of the liquid 1 to be classified and/or the wetted surface area. Precise investigations of the various dependences in which the following aspects also have an influence have shown that the intensity SI has a special curve profile.

The intensity SI is strongly dependent on the following aspects:
conductivity and relative static permittivity of the liquid 1 as already mentioned;
liquid volume FV and the
type of container 101 and/or on the wetted surface area;
type of carrier 103.1;
type of sensor 102;
type of worktable 103.2;
materials of the elements mentioned;
speed of the movement B.

In a liquid level measurement cLLD according to the invention, the jump of the signal a(t) or the signal intensity SI must be significantly greater than all these perturbing influences.

For conductive liquids 1 the signal s(t) or a(t) becomes increasingly smaller closer to the base of the container 101, the smaller the volume FV becomes or the smaller the instantaneously wetted surface area becomes.

The shape (geometry) of the container 101 is also relevant. For example, for the same liquid volume FV the signal intensity SI is higher in a container 101 having a slightly curved base (see, e.g. FIG. 4B) than in a container having a V-shaped base (see, e.g. FIG. 8B).

According to the invention even the smallest volumes should be made measurable/detectable. That is, the limits of the feasible should be shifted in the direction of small volumes FV. Preferably volumes FV which are smaller than 10 µl and preferably smaller than 5 µl should be detectable.

In order to achieve good results in a capacitive liquid level measurement cLLD according to the invention, in all embodiments the material of the container 101 should be non-conductive and the base of the container 101 can contact the earthed worktable 103.2 or be close thereto (distance AB<2 mm, see FIG. 4B).

Preferably in all embodiments, special carriers 103.1 are used which are optimized for a capacitive liquid level measurement cLLD. Such a carrier 103.1 should fulfil one or more of the following criteria (reference is made here to the example of FIG. 4B):
the carrier walls 103.3 are designed to be non-conductive;
the carrier base 103.4 is designed to be conductive and earthed (for example, together with the worktable 103.2 as shown schematically in FIG. 4B);
the carrier base 103.4 is designed so that it is located close to the liquid 1.

FIG. 4C shows a perspective view of an exemplary carrier 103.1 which is here fitted with 12 tubes 101. In this diagram the base 103.4 of the carrier 103.1 and the walls 103.3 can be clearly seen. The carrier base 103.4 can for example be connected to the working area 103.2 so that it is earthed together with the working area 103.2.

All in all, the following rules or approaches should be taken into account if particularly reliably and precisely operating devices 100 or processes 200 are to be provided.
The threshold value is related to the jump in the capacitance (signal jump) which occurs during immersion (or emergence).
The threshold value must be balanced between the sensitivity with respect to the liquid 1 and the lack of sensitivity with respect to the environment (e.g. the container environment 103).
If the threshold value is set too low, the liquid level measurement cLLD becomes increasingly sensitive. As a result, incorrect measurements become more probable.
If the threshold value is set too high, the liquid level measurement cLLD becomes increasingly insensitive. That is, the sensor 102 must be inserted more deeply into the liquid 1 (missing of a liquid level) before the capacitance jump is sufficiently large to be able to be detected. In addition, liquids 1 with weak conductivity can then no longer be detected.

Figure 6A:
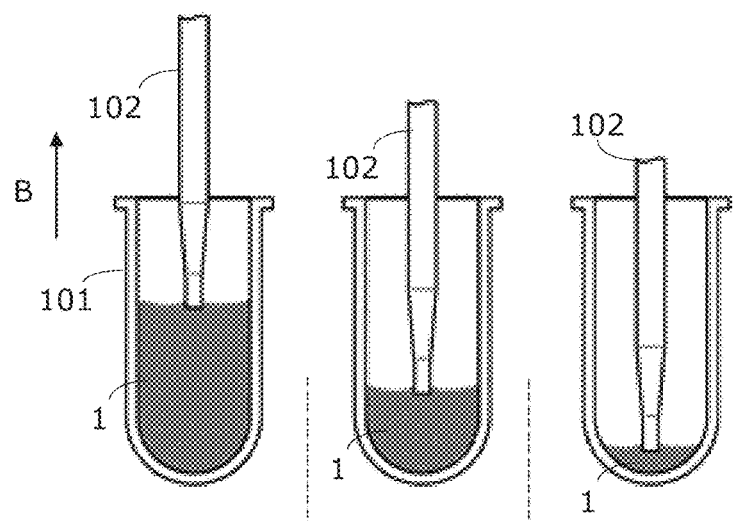
FIG. 6A shows a schematic view of three identical containers which are each filled with different liquid volumes.
Figure 6B:
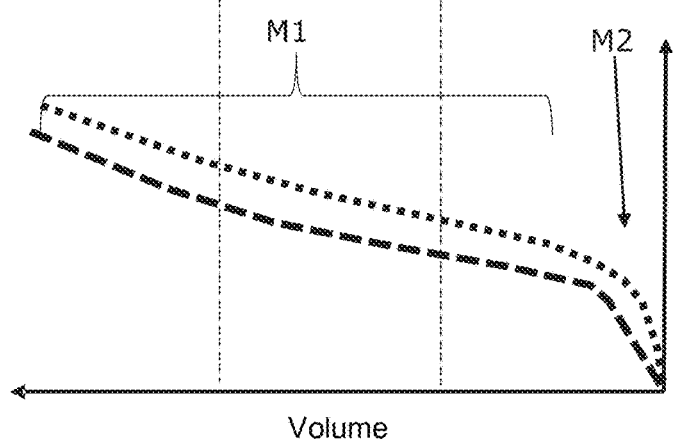
FIG. 6B shows a schematic diagram which is related to the three filling level situations shown in FIG. 6A, where on the one hand the signal intensity is shown on emergence of the sensor from a conductive liquid and on the other hand suitable threshold values.

FIG. 6A shows a schematic view of three identical containers 101 which are each filled with different liquid volumes FV. The liquid volume FV decreases from left to right. FIG. 6B shows a schematic diagram which is related to the three fill level situations shown in FIG. 6A. This diagram shows on the one hand the signal intensity SI during emergence of the sensor 102 from a conducting liquid 1 and on the other hand suitable threshold values.

Some of the statements already made above can be confirmed from these figures. The intensity SI decreases as the liquid volume FV becomes smaller or with decreasing wetted surface area. The intensity curve (upper curve in FIG. 6B) has a distinct first region M1 which is monotonically decreasing and which can be approximated by a straight line having a constant gradient. The intensity curve also has a second region M2 which is strongly decreasing and whose gradient increases. No measurement results are available for very small volumes FV.

According to the invention, preferably in all embodiments within the framework of the automated classification, each value of the intensity curve is assigned a corresponding threshold value. In order that signals remain detectable during immersion or emergence in a liquid level measurement cLLD, the associated threshold value must always be slightly lower than the values of the intensity curve. In FIG. 6B the lower curve represents a possible profile of a threshold value curve.

Figure 7:
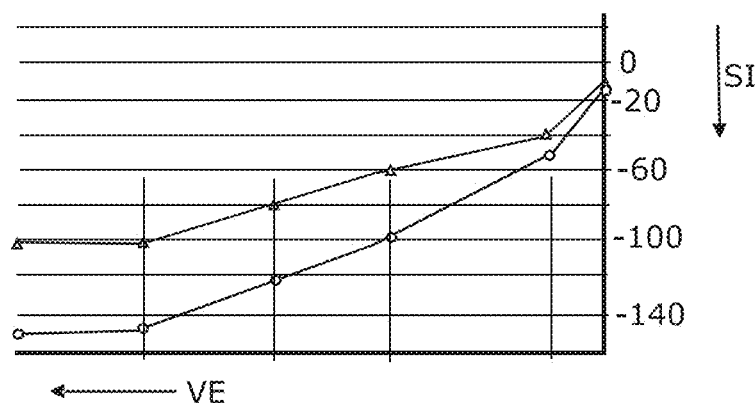
FIG. 7 shows a schematic diagram which shows a series of discrete threshold values which are suitable for carrying out a capacitive liquid level measurement (cLLD) which evaluates a first faster and a second slower signal.

According to the invention, preferably in all embodiments a series of discrete threshold values is determined (as shown, e.g. in FIG. 7). In all embodiments however a threshold value function sV(FV) or sV(bO) can be determined where the threshold value function sV(FV) has a dependence on the liquid volume FV or the threshold value function sV(bO) has a dependence on the wetted surface area of the liquid 1 in the container 101.

Preferably in all embodiments the liquid level measurement cLLD is performed so that the liquid volume FV to be measured and/or the instantaneous wetted surface area have/has an influence on the choice of the threshold value. With decreasing liquid volume FV or with decreasing wetted surface area, the threshold value preferably also decreases. Consequently the sensitivity of the cLLD liquid level measurement becomes increasingly lower.

FIG. 7 shows a schematic diagram which shows a series of discrete threshold values which are suitable for performing a capacitive liquid level measurement cLLD which evaluates a first faster signal s1(t) and a second slower signal s2(t) (see also FIG. 5). The volume units are plotted on the x axis and the signal intensity SI is plotted on the y axis. With increasing volume FV the signal jump during immersion or emergence becomes increasingly greater, i.e. the intensity SI increases. Accordingly the threshold values also become increasingly larger.

Preferably in all embodiments which operate with two signals s1(t), s2(t) threshold value curves are used whose profile for both signals is identical or similar (as shown in FIG. 7). The threshold value curve for the faster signal s1(t) is designated by vSs and the threshold value curve for the slower signal s2(t) is designated with vSl. Preferably in all embodiments it holds that vSl>vSs (as also shown in FIG. 5).

Figure 8B:
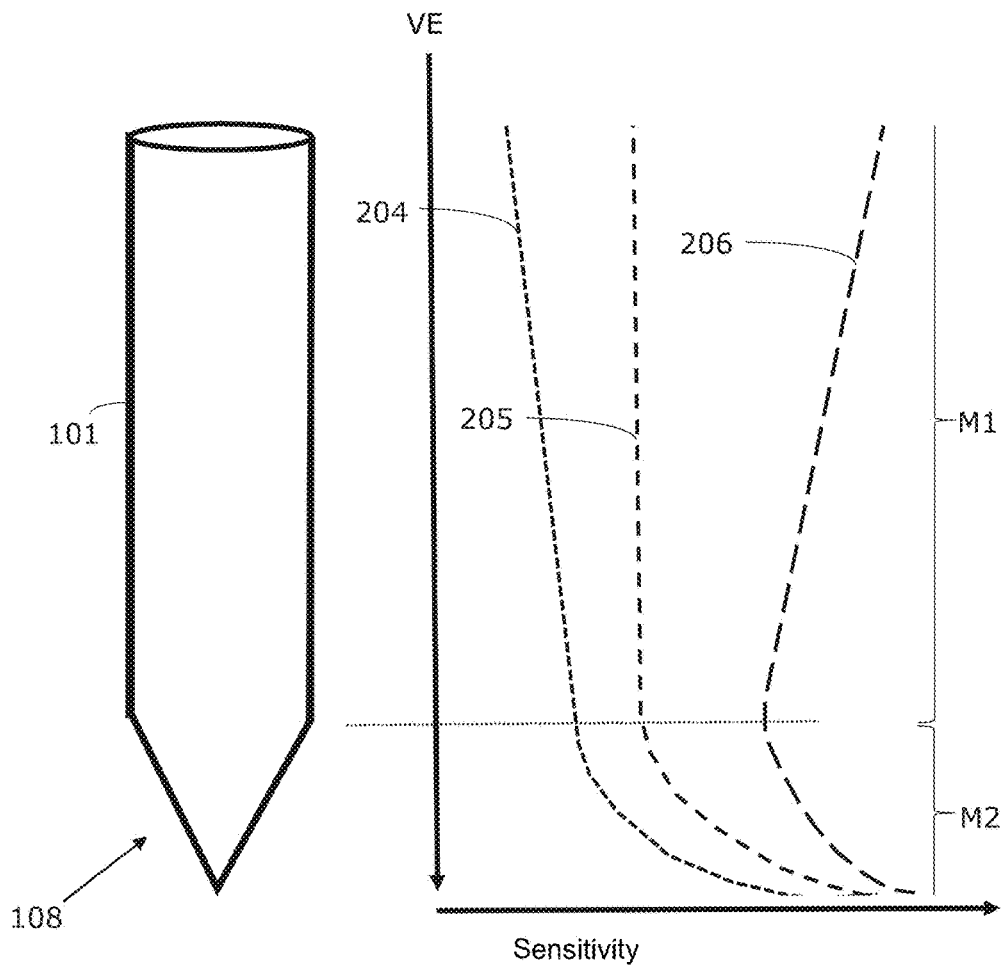
FIG. 8B shows a highly schematic diagram which is related to a container shown on the left where a curve is predefined for each of three liquid classes in the diagram.

FIG. 8A shows a highly schematic diagram which is related to a container 101 shown on the left, which here has a slightly curved base 108. In this diagram a curve 201, 202, 203 is predefined for each of three liquid classes which are shown in schematic form in FIG. 8A. In the diagram the volume unit VE is plotted as a function of the sensitivity. It can also be seen here that for the liquids of all three sensitivity classes 1st Cl., 2nd Cl. and 3rd Cl., the sensitivity must decrease significantly with decreasing volume FV (or with decreasing wetted surface area) in order to be able to perform successful liquid level measurements cLLD. The three curves 201, 202, 203 can be the same or similar, as shown in FIG. 8A. However, the three curves can also be significantly different, as shown in FIG. 8B.

FIG. 8B shows a highly schematic diagram which is related to a container 101 shown on the left, which here has a V-shaped tapering base 108. The V-shaped base 108 is particularly clearly defined here in order to show a situation in which the dependence of the curve profiles on the wetted surface area can be clearly identified. As in FIG. 8A the three sensitivity classes 1st Cl., 2nd Cl. and 3rd Cl. are shown. For a liquid having particularly good conductivity (3rd Cl.), the corresponding curve 204 has a monotonically slightly increasing profile (which, for example, in the region M1 can be linearly ascending). In the region of the transition from the purely cylindrical region of the container 101 to the tapering base 108, the curve 204 has a curved profile with clearly increasing slope (region M2 in FIG. 8B). The curve 205 of the good conducting liquid (2nd Cl.) has a rectilinear profile which has no slope and no gradient or whose slope or gradient is very small (region M1 in FIG. 8B). For the curve 206 of the poorly conducting liquid (1st Cl.) the curve 206 tilts towards the right in the schematic diagram of FIG. 8B. This curve 206 has a rectilinear profile with a gradient in the region M<2 in FIG. 8B. The tilting of the curve 206 to the right can explained in a simplified manner in that for a poorly conducting liquid the size of the wetted area in the region M1 of the curve 206 does not play any role. In this region the distance AB from the worktable 103.2 is significantly more dominant.

It can be deduced from FIG. 8B that the sensitivity curves of various liquids can certainly have a different profile. Therefore the threshold value curves can also have a different profile according to the conductivity of the liquid.

Preferably two and particularly preferably three sensitivity classes 1st Cl., 2nd Cl., and 3rd Cl., can be predefined (see also FIGS. 8A and 8B). These sensitivity classes 1st Cl., 2nd Cl., and 3rd Cl. can be defined as follows, for example:

Conductive liquids having a conductivity <10 μS and relative static permittivity between 24 and 80 (poor conductivity: 1st Cl.)

Conductive liquids with conductivity <10 μS and relative static permittivity >80 (good conductivity 2nd Cl.)

Conductive liquids with conductivity >100 μS (very good conductivity 3rd Cl.).

| Reference list: | |
|---|---|
| Liquid | 1 |
| Charging/discharging circuit | 2 |
| Pipette tip | 3 |

-continued

| Reference list: | |
|---|---|
| Base plate | 4 |
| Container | 5 |
| Signal processing circuit | 6 |
| Controller | 7 |
| Laboratory apparatus | 10 |
| Input side | 11 |
| Switch/actuator | 12 |
| Device | 100 |
| Container (Labware) | 101 |
| Sensor | 102 |
| Carrier/support | 103.1 |
| Worktable/surface/base plate | 103.2 |
| Carrier wall | 103.3 |
| Carrier base | 103.4 |
| Container environment | 103 |
| Classification module | 104 |
| Line connection | 105 |
| Circuitry connection | 106 |
| Memory | 107 |
| Base | 108 |
| Liquid level measurement system | 110 |
| Method | 200 |
| Curves | 201, 202, 203, 204, 205, 206 |
| Output signal of cLLD | a(t) |
| Distance | AB |
| Delivery movement | B |
| Liquid level measurement | cLLD |
| Capacitance between sensor and liquid | $C_{tip/liq}$ |
| Series capacitance | $C_{coupl}$ |
| Permittivity | $\varepsilon$ |
| Frequency-dependent permittivity | $\varepsilon(\omega)$ |
| Field constant | $\varepsilon_0$ |
| Control variable or signal | e |
| First sensitivity | E1 |
| Second sensitivity | E2 |
| Liquid volume | FV |
| Process steps | S1, S2, S3, S4, S5, S6 |
| Output signal/(detection) signal | s(t) |
| (Signal) intensity | SI |
| Sensitivity class | Kl |
| First range | M1 |
| Second range | M2 |
| Time | t |
| First threshold value | sV1 |
| Second threshold value | sV2 |
| Threshold value function as a function of liquid volume | sV(FV) |
| Threshold value function as a function of wetted surface area | sV(bO) |
| Volume units | VE |
| Predefined threshold value | vS |
| Predefined threshold value fast signal | vSs |
| Predefined threshold value slow signal | vSl |
| Admittance | Y |
| Complex quantity/impedance | Z |

The invention claimed is:

1. Method (200) for the automated classification of a liquid (1) in a device (100), which is designed to make a capacitive liquid level measurement (cLLD) of the liquid (1) in a container (101), wherein the method (200) comprises the following steps:

providing the liquid (1) in a container (101), providing a line connection (105) between a classification module and a sensor 102 which can be operated at different sensitivities, performing a capacitive measurement of this liquid (1)
when executing an immersion movement of the sensor (102) into the liquid (1) or
when executing an emerging movement of the sensor (102) out from the liquid (1),
wherein a signal jump of a signal (s(t)) of the capacitive measurement is processed which is formed during the immersion movement of the sensor (102) into the liquid (1) or during the emerging movement of the sensor (102) from the liquid (1) in order to perform the automated classification of the liquid (1).

2. The method (200) according to claim 1, characterized in that the intensity (SI) of the signal (s(t)) in the region of the signal jump and/or the amplitude of the signal jump are processed in order to perform the automated classification of the liquid (1).

3. The method (200) according to claim 1 or 2, characterized in that the following steps are executed for the automated classification of the liquid (1):
classification (S4) of the liquid (1) into a first sensitivity class if the signal jump of the signal (s(t)) of the capacitive measurement lies above a predefined threshold value (vS),
classification (S5) of the liquid (1) into a second sensitivity class if the signal jump of the signal (s(t)) of the capacitive measurement lies below the predefined threshold value (vS).

4. The method (200) according to claim 1 or 2, characterized in that the automated classification of the liquid (1) is made with the aid of desired values which were determined in a predefined determination environment of the device (100) and then stored.

5. The method (200) according to claim 4, characterized in that the automated classification of the liquid (1) is accomplished in a defined classification environment of the device (100), wherein the classification environment is identical to the determination environment at least with reference to one of the following specifications:
the liquid volume (FV) of the liquid (1) in the container (101),
surface area wetted by the liquid (1) in the container (101),
the type of sensor (102),
the type of container (101),
the type of carrier (103.1) for the container (101),
the type of worktable (103.2) on which the carrier (103.1) is disposed.

6. The method (200) according to claim 1 or 2, characterized in that a dedicated sample container serves as container (101) which is filled with a known liquid volume (FV) of the liquid (1), wherein a processor-controlled procedure for automated determination of the sensitivity of this liquid (1) is executed for automated classification of the liquid (1).

7. The method (200) according to claim 6, characterized in that within the framework of this procedure the sensor (102) is immersed from a position above a level of the liquid (1) in the dedicated sample container into the liquid (1), wherein during immersion of the sensor (102) the capacitive measurement (cLLD) is executed and wherein by means of a capacitance change which is obtained during immersion either a sensitivity value is determined for this liquid (1) or the liquid (1) is classified into a sensitivity class by means of a comparison with predefined quantities.

8. The method (200) according to claim 1 or 2, characterized in that within the framework of the capacitive measurement a plurality of sensors (102) consecutively execute an immersion movement into the container (101), wherein during immersion of a first sensor (102) a first signal jump or a first intensity value and during immersion of a second sensor (102) a second signal jump or a second intensity value are determined and wherein an average value is formed from the two signal jumps or the two intensity values.

9. The method (200) according to claim 1 or 2, characterized in that within the framework of the capacitive measurement for the liquid (1)
a threshold value (vS1; vS2) and/or
a series of discrete threshold values (vS1; vS2) and/or
a threshold value function (vS(FV); vS(bO)) is/are determined, wherein the threshold value function (vS(V); vS(bO)) has a dependence on the liquid volume (FV) of the liquid (1) in the container (101) or on the wetted surface area in the container (101).

10. The method (200) according to claim 1 or 2, characterized in that in a subsequent step in the device (100) a capacitive liquid level measurement (cLLD) is performed using a signal (s(t); s1($t$), s2($t$)) which is provided by the sensor (102) wherein for this capacitive liquid level measurement (cLLD) an adjustment of the sensitivity (E1, E2) of the capacitive liquid level measurement (cLLD) is automatically made by means of the previously accomplished classification.

11. The method (200) according to claim 3, characterized in that the automated classification of the liquid (1) is made with the aid of desired values which were determined in a predefined determination environment of the device (100) and then stored.

12. The method (200) according to claim 3, characterized in that a dedicated sample container serves as container (101) which is filled with a known liquid volume (FV) of the liquid (1), wherein a processor-controlled procedure for automated determination of the sensitivity of this liquid (1) is executed for automated classification of the liquid (1).

13. The method (200) according to claim 5, characterized in that a dedicated sample container serves as container (101) which is filled with a known liquid volume (FV) of the liquid (1), wherein a processor-controlled procedure for automated determination of the sensitivity of this liquid (1) is executed for automated classification of the liquid (1).

14. The method (200) according to claim 3, characterized in that within the framework of the capacitive measurement a plurality of sensors (102) consecutively execute an immersion movement into the container (101), wherein during immersion of a first sensor (102) a first signal jump or a first intensity value and during immersion of a second sensor (102) a second signal jump or a second intensity value are determined and wherein an average value is formed from the two signal jumps or the two intensity values.

15. The method (200) according to claim 5, characterized in that within the framework of the capacitive measurement a plurality of sensors (102) consecutively execute an immersion movement into the container (101), wherein during immersion of a first sensor (102) a first signal jump or a first intensity value and during immersion of a second sensor (102) a second signal jump or a second intensity value are determined and wherein an average value is formed from the two signal jumps or the two intensity values.

16. The method (200) according to claim 3, characterized in that within the framework of the capacitive measurement for the liquid (1)
a threshold value (vS1; vS2) and/or
a series of discrete threshold values (vS1; vS2) and/or
a threshold value function (vS(FV); vS(bO)) is/are determined, wherein the threshold value function (vS(V);

vS(bO)) has a dependence on the liquid volume (FV) of the liquid (1) in the container (101) or on the wetted surface area in the container (101).

17. The method (200) according to claim 5, characterized in that within the framework of the capacitive measurement for the liquid (1)

a threshold value (vS1; vS2) and/or a series of discrete threshold values (vS1; vS2) and/or a threshold value function (vS(FV); vS(bO)) is/are determined, wherein the threshold value function (vS(V); vS(bO)) has a dependence on the liquid volume (FV) of the liquid (1) in the container (101) or on the wetted surface area in the container (101).

18. The method (200) according to claim 3, characterized in that in a subsequent step in the device (100) a capacitive liquid level measurement (cLLD) is performed using a signal (s(t); s1(t), s2(t)) which is provided by the sensor (102) wherein for this capacitive liquid level measurement (cLLD) an adjustment of the sensitivity (E1, E2) of the capacitive liquid level measurement (cLLD) is automatically made by means of the previously accomplished classification.

19. The method (200) according to claim 5, characterized in that in a subsequent step in the device (100) a capacitive liquid level measurement (cLLD) is performed using a signal (s(t); s1(t), s2(t)) which is provided by the sensor (102) wherein for this capacitive liquid level measurement (cLLD) an adjustment of the sensitivity (E1, E2) of the capacitive liquid level measurement (cLLD) is automatically made by means of the previously accomplished classification.

\* \* \* \* \*